US005685988A

United States Patent [19]

Malchesky

[11] Patent Number: 5,685,988
[45] Date of Patent: Nov. 11, 1997

[54] DIALYSIS PROCESS AND SYSTEM

[76] Inventor: Paul Malchesky, 239 Barrington Ridge, Paynesville, Tsp., Ohio 44077

[21] Appl. No.: 120,747

[22] Filed: Sep. 15, 1993

[51] Int. Cl.$^6$ .......................... A61M 1/14; B01D 61/00; B01D 61/30; B01D 61/32
[52] U.S. Cl. ..................... 210/646; 210/85; 210/195.2; 210/645; 210/805; 210/929; 604/4
[58] Field of Search ................................ 210/645, 646, 210/651, 739, 746, 805, 85, 195.2, 96.1, 252, 321.71, 321.72, 929; 604/4, 5; 324/439, 443, 555

[56] References Cited

U.S. PATENT DOCUMENTS

| | | | |
|---|---|---|---|
| 3,669,878 | 6/1972 | Marantz et al. | 210/195.2 |
| 3,669,880 | 6/1972 | Marantz et al. | 210/195.2 |
| 3,822,201 | 7/1974 | Waters et al. | |
| 3,926,734 | 12/1975 | Gray et al. | |
| 3,989,622 | 11/1976 | Marantz et al. | |
| 4,036,747 | 7/1977 | Mori et al. | |
| 4,094,775 | 6/1978 | Mueller. | |
| 4,213,859 | 7/1980 | Smakman et al. | 210/259 |
| 4,508,622 | 4/1985 | Polaschegg et al. | 210/321.71 |
| 4,923,613 | 5/1990 | Chevallet | 210/321.71 |
| 4,990,258 | 2/1991 | Bjare et al. | 210/90 |
| 5,024,756 | 6/1991 | Sternby | 210/93 |
| 5,100,554 | 3/1992 | Polaschegg | 210/647 |
| 5,110,477 | 5/1992 | Howard et al. | 210/321.71 |
| 5,308,315 | 5/1994 | Khuri et al. | 210/646 |
| 5,399,157 | 3/1995 | Goux et al. | 604/4 |
| 5,405,315 | 4/1995 | Khuri et al. | 604/4 |
| 5,518,623 | 5/1996 | Keshaviah et al. | 210/646 |

OTHER PUBLICATIONS

L.J. Garred et al., The International Journal of Artificial Organs, vol. 12, No. 2, pp. 96–102 (1989).
Malchesky et al., "Arrangement for the Direct Assessment of Solute Removal During Hemodialysis", Cleveland Clinic Foundation Invention and Discovery Disclosure (Jun., 1990).
"Direct Quantification of Dialysis", P. S. Malchesky, et al., Dialysis & Transplantation, vol. 11, No. 42 (1982) pp. 42–49.
"Urea Kinetic Modelling Based On Monitoring Urea In the Spent Dialysate Stream", L. J. Gerred et al. ASAIO 1990 Abs.
"KT/V & Protein Catabolic Rate Determination From Serial Urea Measurement In The Dialysate Effluent Stream", L. J. Garred et al., Art. Organs, vol. 16, No. 3, 1992, pp. 248–255.

*Primary Examiner*—John Kim
*Attorney, Agent, or Firm*—Jim Zegeer, Esq.

[57] ABSTRACT

Disclosed is a method and apparatus for the quantification of solute removal during hemodialysis. The method relies upon discontinuing the flow of fresh dialysate to the dialyzer and recirculating the dialysate in a closed loop through the dialyzer. Recirculation is continued until a steady state concentration of solute (e.g. urea) in the dialysate is achieved. Analysis of the dialysate by suitable means at this time yields a value equal to the solute concentration in the blood without the need for blood sampling. Normal dialysis is resumed by discontinuing the recirculation and providing fresh dialysate to the dialyzer. Determination of solute concentrations at least at the beginning and end of the dialysis period allows the determination of solute loss and the quantification of dialysis therapy and its on-line prescription.

6 Claims, 3 Drawing Sheets

DIALYSIS PROCESS AND SYSTEM

BACKGROUND OF THE INVENTION

This invention relates to a recirculating dialysate system to allow the direct on-line assessment of solute removal during hemodialysis. Renal dialysis is a medical intervention for insufficient function or complete failure of the kidney(s). In this procedure an external man-made kidney is plumbed into the bloodstream to remove impurities and to cleanse the blood. This is done by shunting a portion of the patient's blood through an extracorporeal blood circuit having as an integral part the artificial kidney device. The dialysis session or treatment time can be as long as ten (10) hours but is more typically two to five hours. In contrast to other kinds of extracorporeal treatments, such as blood perfusion or plasmapheresis, hemodialysis involves repeated thrice weekly contacts of the patient's blood with foreign man-made surfaces and this treatment mode may go on for years. Renal dialysis with an extracorporeal kidney substitute can be life saving but there are physiological changes, some of which can be deleterious.

While many of these changes can be attributed to the procedure itself (i.e. the removal of essential molecules such as amino acids and hormones sometimes resulting in malnutrition) of equal importance is the interaction of the materials of the dialysis circuit with blood, with the dialysis unit itself presenting by far the largest area to the blood. Therefore, it is of importance to not "over dialyze" a patient. Of even greater importance is the problem of delivering too little dialysis and the lack of a methodology to indicate this. Such factors as a patient's general health and, especially, his diet and also the minute-to-minute efficiency of the dialyzer module can effect the need for continuing or stopping the dialysis session.

As mentioned above, hemodialysis is an accepted form of treatment for certain diseases of the kidney especially chronic renal failure. As represented schematically in FIG. 1, the process involves flowing a fraction of the patient's blood through an extracorporeal circuit containing an "artificial kidney" or dialyzer. The dialyzer incorporates a semipermeable membrane, most typically in hollow fiber form, which separates the blood and dialysate streams. The prescription of dialysis therapy varies throughout the world, nephrologists are guided by several factors including patient symptoms, predialysis urea (BUN) or creatinine analysis and in some cases kinetic modelling.

In spite of these efforts, many of the 60 million annual procedures are performed with little knowledge of the per treatment efficiency as related to individual patient's needs. There is a need for a methodology that can routinely be applied to ascertain that prescribed dialysis is in fact being delivered, and to aid in quality assurance assessment in dialysis. More particularly, there is a need to determine efficiency of impurity removal e.g., in terms of solute loss, so as to permit the quantification of dialysis therapy and its on-line prescription.

SUMMARY OF THE INVENTION

In accordance with this invention, there is provided apparatus and method for monitoring the progress and efficiency of the dialysis process, especially hemodialysis.

More particularly, there is provided apparatus and method for determining the concentration of toxic substances and impurity removal in the bloodstream without the requirement for blood sampling.

The advantages and benefits of this invention minimizes patient discomfort by monitoring the progress of dialysis so as to support dietary counseling and provide time based assessments (days to weeks to years) of dialytic and dietary needs.

To achieve these and other advantages and benefits, apparatus and method is disclosed herein to monitor the progress of dialysis by determination of solute concentration in the dialysate. At the beginning of the dialysis period the flow of fresh dialysate to the dialyzer is discontinued, and the dialysate is recirculated in a closed loop through the dialyzer. Recirculation is continued until concentration equilibrium is achieved between the solute in the patient's blood and in the dialysate loop. Analysis of the dialysate by suitable means at this time yields a value for the "pre" blood solute concentration without the need for blood sampling. Normal dialysis is resumed by discontinuing recirculation and delivering fresh dialysate to the dialyzer. A return to the recirculation mode at any time during the dialysis period and at the prescribed end of the dialysis session allows a determination of total solute loss and an assessment of dialysis therapy. Because the prescribed end may not be the desired end of dialysis therapy, this invention permits quantification of the dialysis therapy and on-line prescription decisions to be made about continuing or ending the therapy, thereby improving the quality management of patients. In the best embodiment of this invention, assessment of urea content is a specific application of this invention.

DETAILED DESCRIPTION OF THE PREFERRED EMBODIMENT

Figure 1:
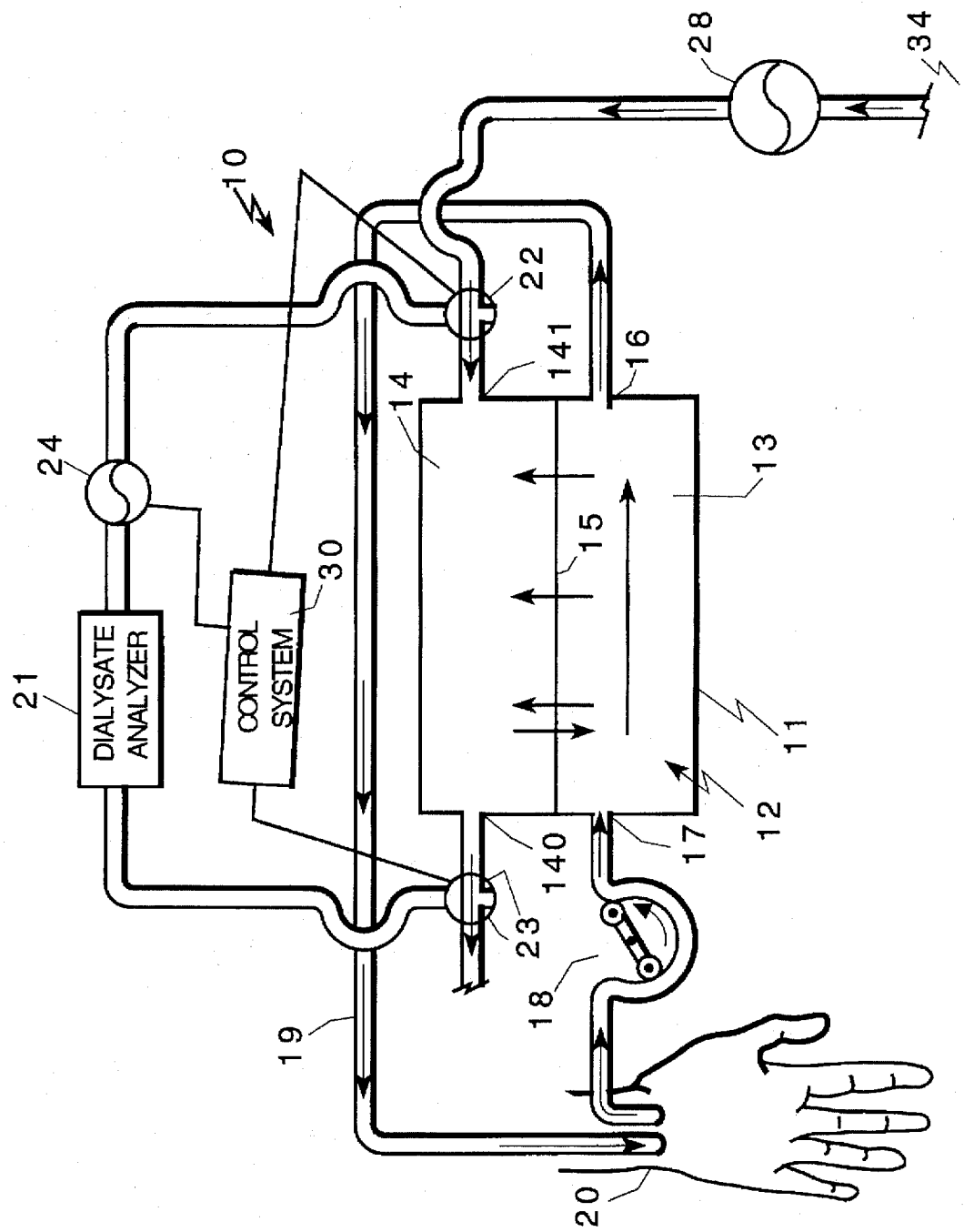
FIG. 1 is a schematic representation of a single pass, single patient dialysis system incorporating a modification to allow recirculation of the dialysate within the dialyzer to achieve the present invention.

FIG. 1 shows a schematic of a single pass, single patient hemodialysis system 10 which incorporates the present invention. Dialyzer 11 has a chamber 12 divided into a blood flow chamber portion 13 and a dialysate chamber portion 14 by dialyzing membrane 15. Blood input and output ports 16 and 17 are connected to blood pump 18 and blood return loop 19, respectively, for extracting blood from patient 20 and returning dialyzed blood to the patient 20. Dialysate input port 14-I and dialysate output port 14-O are selectively connected to the fresh dialysate supply and waste or to the recirculation loop of this invention. The invention permits recirculation of the dialysate within the dialyzer 11 and incorporates a urea analyzer 21 (as noted above, analyzers for solutes other than urea can be used) placed in the recirculation loop which includes three-way valves 22 and 23 and dialysate recirculation pump 24. Valves 22 and 23 are automatically operated simultaneously to connect the recirculation loop to the dialyzer preferably before the recirculation pump is turned on by control system 30, while the fresh dialysate pump is turned off.

Figure 2:
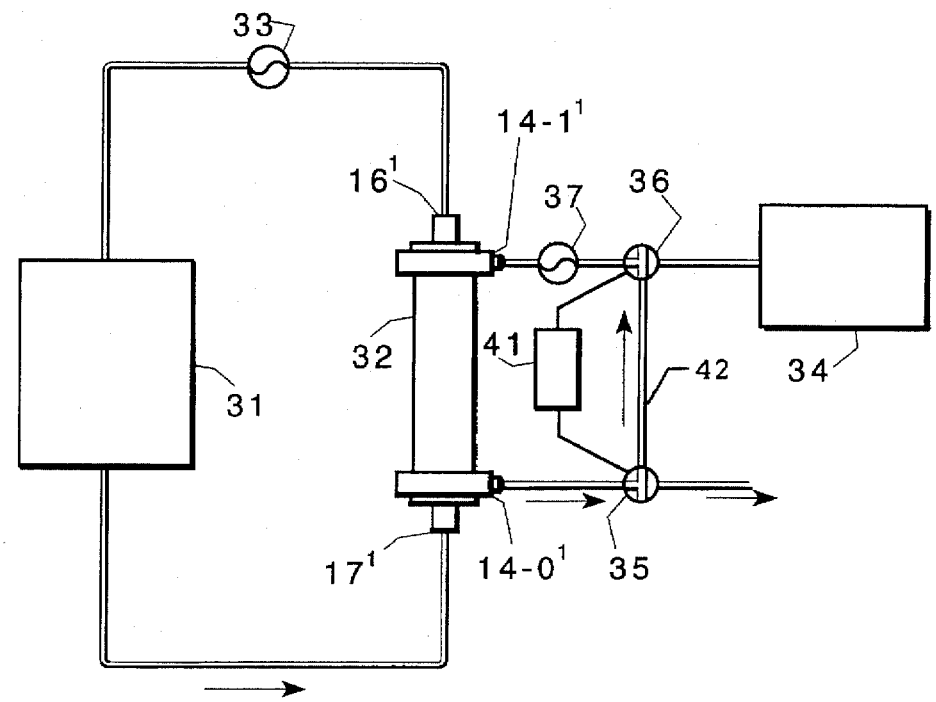
FIG. 2 is a schematic representation of a model system of the present invention.

In the embodiment shown in FIG. 2, the dialysate pump 37 is in the recirculation loop when valves 35 and 36 are in the position shown and connected to the dialysate reservoir or supply source 34. Through recirculation of the dialysate the concentration of urea in the dialysate quickly rises to become equal to that of the blood. Thus, according to one aspect of the invention, if recirculation is practiced at the beginning of the session, the initial blood urea concentration can be determined without the need for sampling blood. Likewise, at the end of the dialysis period, the dialysate may be recirculated and the final blood concentration determined. At any point during the dialysis period, the blood urea concentration may be determined by going into the recirculation mode.

The time to achieve equilibration between the blood and dialysate is highly dependent upon the permeability of the membrane, blood and dialysate flow rates, and the volume of the dialysate recirculation circuit. The latter concepts are best illustrated by reference to FIGS. 2 and 3 where experimental results are presented from a model system. A (70 kG) adult dialysis patient is modelled by 35 L of a solution of urea in physiological saline 31. A urea nitrogen level of between 90 and 100 mg/dL was chosen and the continuously stirred solution was circulated through the blood side of the dialyzer 32 at a constant rate of 300 mL/min. by means of a peristaltic pump 33. A bicarbonate dialysate solution from reservoir 34 (Naturalyte 9000) was pumped by pump 37 at 500 mL/min. through the shell side of the hollow fiber dialyzer (Travenol CF15.11). In a normal dialysis mode the dialysate was allowed to go to waste or alternatively, by means of the three-way valves 35 and 36 provided by this invention and shown in FIG. 2, could be selectively recirculated. Control system 41 simultaneously operates valves 35 and 36 to insert or connect recirculation to the dialysate chamber portion of dialyzer 32. The volume of the recirculation loop including dialyzer and pump 37 was 65 mL. A small sampling port 42 was included in the recirculation loop for withdrawal of samples (0.1 mL) for urea analysis. A urea nitrogen diagnostic kit (Sigma Chemical Co. 67-10) was used for this purpose. Any suitable means of analysis could be used including an on-line urea analyzer as disclosed in U.S. Pat. No. 3,926,734.

Figure 3:
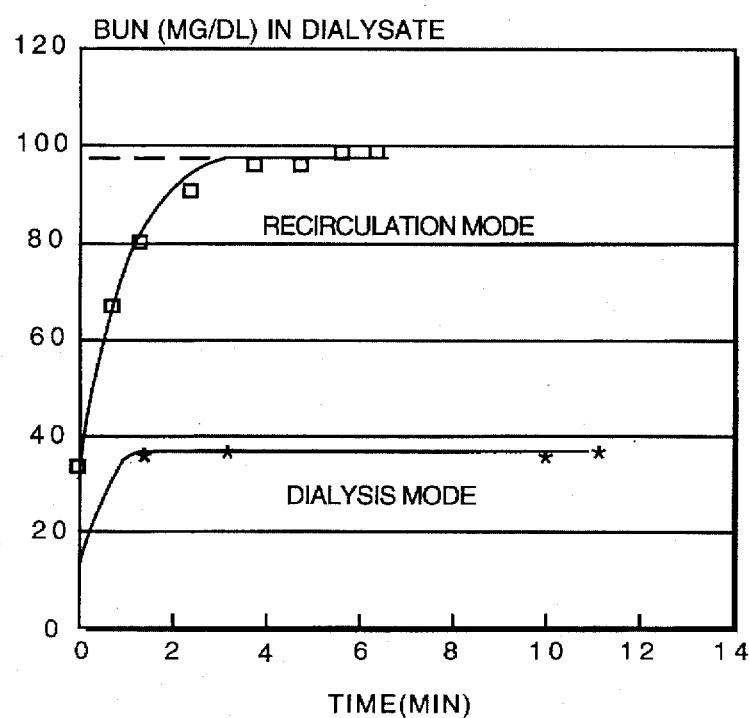
FIG. 3 is a graphical representation of the time to achieve equilibrium between blood and dialysate in the system of FIG. 2, FIGS. 4 and 5 are graphical representations of urea removal during a model dialysis session monitored by the apparatus and methodology of the present invention.

Referring now to FIG. 3, the lower curve was produced when the model system was operated in the normal dialysis mode previously described. A urea nitrogen concentration of 30–35 mg/dL was rapidly established in the dialysate. The upper curve follows the increase in urea concentration in the dialysate as the system was switched to the recirculation mode. Equilibrium with the patient blood urea concentration was reached in less than 3 minutes. Dialysate urea concentrations fall back to their original values in less than 30 seconds upon resuming normal dialysis.

Figure 4:
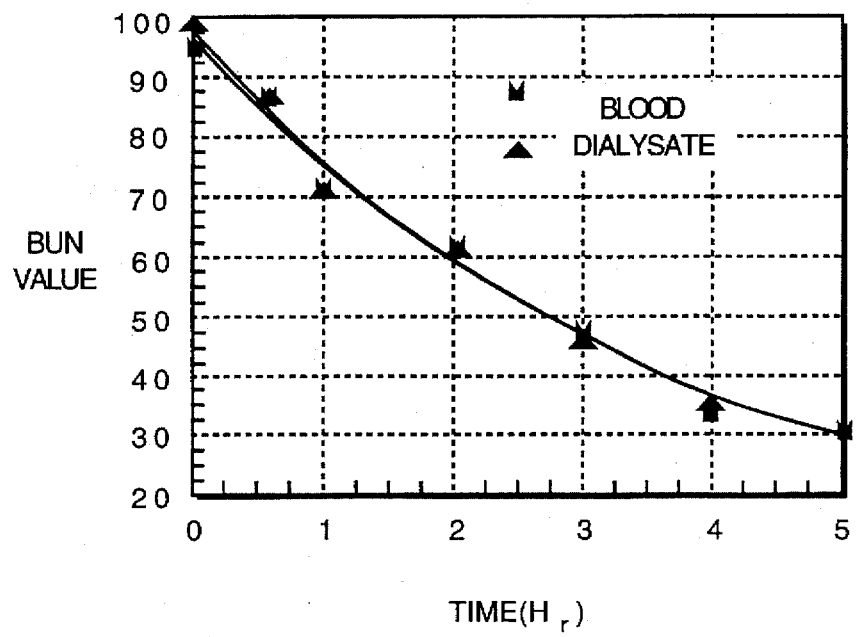
Figure 5:
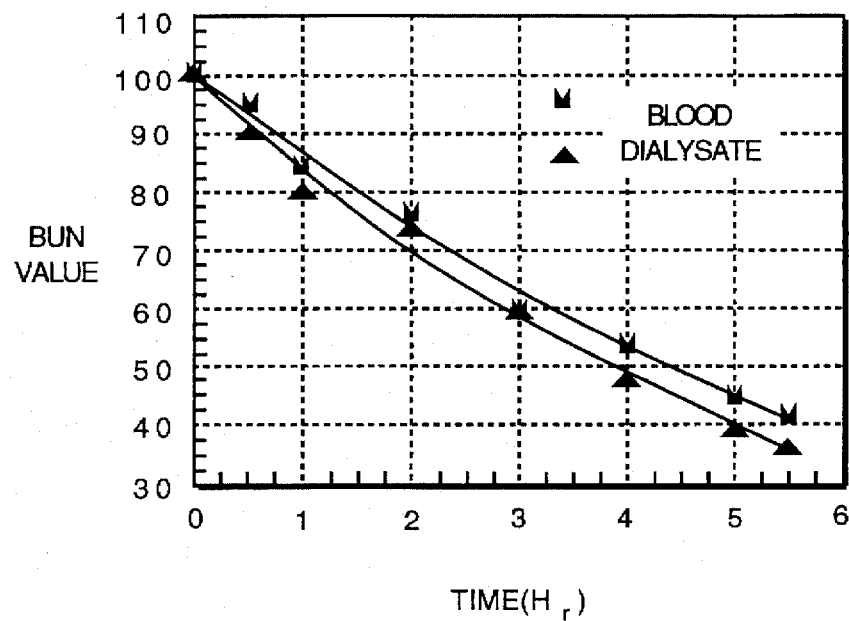

FIG. 4 illustrates how the course of a dialysis session can be monitored by means of the present invention. Using the model system previously described in FIG. 2 dialysis was continued over a five hour period. At regular intervals, recirculation of dialysate was performed for 3 minutes at which point samples of both dialysate and "blood" were taken and analyzed for urea content (BUN). The graph shows data obtained by manual analysis of the samples. The graph shown in FIG. 5 was obtained by on-line analysis of the dialysate by the method described in U.S. Pat. No. 3,926,734.

While preferred embodiments of the invention have been shown and described, it will be appreciated that various modifications and adaptations of the invention will be apparent to those skilled in the art.

What is claimed is:

1. In a dialysis process incorporating a dialyzer for the removal of impurities from a flowing supply of blood to a flowing supply of fresh dialysate from a main supply of dialysate by means of a dialysis membrane separating the flowing supply of blood from flowing supply of fresh dialysate, the improvement comprising:

providing a closed dialysate recirculation loop, discontinuing the flow of fresh dialysate to the dialyzer and recirculating the dialysate in said closed dialysate recirculation loop isolated from the main supply of dialysate until concentration equilibrium has been established between a solute in the blood and in the closed dialysate recirculation loop, analyzing the contents of the closed dialysate recirculation loop to determine the solute concentration, discontinuing recirculation in said closed dialysate recirculation loop and providing a flow of fresh dialysate to the dialyzer to continue normal dialysis, repeating the recirculation process at the end of the dialysis period to determine solute loss so as to permit the quantification of dialysis therapy and provide on-line prescription.

2. The dialysis process defined in claim 1 wherein said closed dialysate recirculation loop includes a urea analyzer and said solute concentration is determined automatically without sampling any blood.

3. In a hemodialysis system having a dialyzer, means for providing a supply of dialyzer fluid to said dialyzer and means for circulating blood from a patient through said dialyzer and back to the patient, and means for removing dialyzer-fluid from said dialyzer, the improvement comprising:

a dialyzer fluid recirculation passage connected to said dialyzer for recirculating at least some of the removed dialyzer fluid through said dialyzer one or more times, and an analyzer for analyzing dialyzer fluid in said recirculation passage.

4. The hemodialysis system defined in claim 3 wherein said analyzer includes means to detect concentration equilibrium between a solute in the blood and in the dialysis fluid.

5. The hemodialysis system defined in claim 3 wherein said analyzer is adapted to determine the urea content in the dialyzer fluid in said recirculation passage.

6. The hemodialysis system defined in claim 4 wherein said solute is urea.

* * * * *